US00PP18272P2

(12) United States Plant Patent
Klemm

(10) Patent No.: US PP18,272 P2
(45) Date of Patent: Dec. 4, 2007

(54) ***OSTEOSPERMUM* PLANT NAMED 'KLEO04110'**

(50) Latin Name: *Osteospermum ecklonis*
Varietal Denomination: KLEO04110

(75) Inventor: Nils Klemm, Stuttgart (DE)

(73) Assignee: Klemm + Sohn GmbH + Co. KG, Stuttgart (DE)

( * ) Notice: Subject to any disclaimer, the term of this patent is extended or adjusted under 35 U.S.C. 154(b) by 0 days.

(21) Appl. No.: 11/343,878

(22) Filed: Jan. 31, 2006

(51) Int. Cl.
*A01H 5/00* (2006.01)

(52) U.S. Cl. ..... Plt./360
(58) Field of Classification Search ..... Plt./360
See application file for complete search history.

(56) References Cited

PUBLICATIONS

UPOV–ROM GTITM, Plant Variety Database, 2006/03, GTI Jouve Retrieval Software, citation for 'KLEO04110'.*

COPF Newsletter, vol. 16, #3, Oct. 2004 (total 4 pages).*

* cited by examiner

*Primary Examiner*—Kent Bell
*Assistant Examiner*—S. B. McCormick-Ewoldt
(74) *Attorney, Agent, or Firm*—C. A. Whealy

(57) ABSTRACT

A new and distinct cultivar of *Osteospermum* plant named 'KLEO04110', characterized by its upright, compact and mounded plant habit; freely branching habit; freely and continuous flowering habit; and inflorescences with red purple-colored ray florets.

1 Drawing Sheet

Botanical designation: *Osteospermum ecklonis.*
Botanical denomination: 'KLEO04110'.

BACKGROUND OF THE INVENTION

The present Invention relates to a new and distinct cultivar of *Osteospermum* plant, botanically known as *Osteospermum ecklonis,* and hereinafter referred to by the name 'KLEO4110'.

The new *Osteospermum* is a product of a planned breeding program conducted by the Inventor in Stuttgart, Germany. The objective of the breeding program was to create freely branching *Osteospermum* cultivars with attractive inflorescences.

The new *Osteospermum* originated from an open-pollination in 2002 of an unnamed proprietary *Osteospermum ecklonis* selection, not patented, as the female, or seed, parent with an unidentified selection of *Osteospermum ecklonis,* as the male, or pollen, parent. The new *Osteospermum* was discovered and selected by the Inventor as a single flowering plant within the progeny of the stated open-pollination grown in a controlled environment in Stuttgart, Germany in May, 2003.

Asexual reproduction of the new *Osteospermum* by terminal vegetative cuttings was first conducted in Stuttgart, Germany in May, 2003. Asexual reproduction by cuttings has shown that the unique features of this new *Osteospermum* are stable and reproduced true to type in successive generations.

SUMMARY OF THE INVENTION

The cultivar KLEO04110 has not been observed under all possible environmental conditions. The phenotype may vary somewhat will variations in environment such as temperature and light intensity without, however, any variance in genotype.

The following traits have been repeatedly observed and are determined to be the unique characteristics of 'KLEO04110'. These characteristics in combination distinguish 'KLEO04110' as a new and distinct *Osteospermum:*

1. Upright, compact and mounded plant habit.
2. Freely branching habit.
3. Freely and continuous flowering habit.
4. Inflorescences with red purple-colored ray florets.

Plants of the new *Osteospermum* differ from plants of the female parent selection primarily in plant size and inflorescence color.

Plants of the new *Osteospermum* differ from plants of the male parent selection primarily in ray floret color.

Plants of the new *Osteospermum* can be compared to plants of the cultivar Wildside, disclosed in U.S. Plant Pat. No. 10,603. In side-by-side comparisons conducted in Stuttgart, Germany, plants of the new *Osteospermum* differed from plants of the cultivar Wildside in the following characteristics:

1. Plants of the new *Osteospermum* were more freely branching than plants of the cultivar Wildside.
2. Plants of the new *Osteospermum* had smaller leaves than plants of the cultivar Wildside.
3. Plants of the new *Osteospermum* were more freely flowering than plants of the cultivar Wildside.
4. Plants of the new *Osteospermum* had larger inflorescences than plants of the cultivar Wildside.
5. Plants of the new *Osteospermum* had more ray florets per inflorescence than plants of the cultivar Wildside.

BRIEF DESCRIPTION OF THE PHOTOGRAPH

The accompanying colored photograph illustrates the overall appearance of the new *Osteospermum* showing the colors as true as it is reasonably possible to obtain in colored reproductions of this type. Colors in the photograph may differ from the color values cited in the detailed botanical description which accurately describe the colors of the new *Osteospermum*. The photograph comprises a side perspective view of a typical flowering plant of 'KLEO04110' grown in an outdoor nursery.

DETAILED BOTANICAL DESCRIPTION

The new *Osteospermum* has not been observed under all possible environmental conditions. The phenotype may vary somewhat with variations in environment such as temperature and light intensity, without, however, any variance in genotype. The aforementioned photograph, following observations and measurements describe plants grown in Stuttgart, Germany in an outdoor nursery during the spring and summer and under commercial production practices. Plants were about four months old when the photographs and description were taken. During the production of the plants, day temperatures ranged from 20° C. to 35° C. and night temperatures ranged from 5° C. to 10° C. Plants were pinched one time about two weeks after planting. In the following description, color references are made to The Royal Horticultural Society Colour Chart, 1995 Edition, except where general terms of ordinary dictionary significance are used.

Botanical classification: *Osteospermum ecklonis* cultivar KLEO04110.

Parentage:

*Female, or seed, parent.*—Unnamed proprietary selection of *Osteospermum ecklonis,* not patented.

*Male, or pollen, parent.*—Unidentified selection of *Osteospermum ecklonis,* not patented.

Propagation:

*Type.*—Terminal vegetative cuttings.

*Time to initiate rooting, summer.*—About 8 days at 25° C.

*Time to initiate rooting, winter.*—About 10 days at 18° C.

*Time to produce a rooted young plant, summer.*—About 18 days at 25° C.

*Time to produce a rooted young plant, winter.*—About 20 days at 18° C.

*Root description.*—Fine, fibrous; white in color.

*Rooting habit.*—Dense.

Plant description:

*Plant form and growth habit.*—Perennial herbaceous container and garden plant. Upright, compact and mounded plant habit; inverted triangle. Freely branching habit, about ten lateral branches per plant.

*Plant height.*—About 17 cm.

*Plant width or area of spread.*—About 30 cm.

*Lateral branches.*—Length: About 16 cm. Diameter: About 3 mm. Internode length: About 2 cm. Aspect: Mostly upright. Strength: Strong. Texture: Smooth, glabrous. Color: Close to 146A.

*Foliage description.*—Arrangement: Alternate, simple. Length: About 3.5 cm. Width: About 1.5 cm. Shape: Oblong. Apex: Obtuse. Base: Attenuate. Margin: Crenate. Venation pattern: Pinnate. Texture, upper and lower surfaces: Smooth, glabrous; leathery. Color: Developing and fully expanded foliage, upper surface: 147B; venation, 148B. Developing and fully expanded foliage, lower surface: 147B; venation, 147C. Petiole length: About 10 cm. Petiole diameter: About 2 mm. Petiole color, upper and lower surfaces: Close to 147B.

Inflorescence description:

*Appearance.*—Solitary terminal and axillary inflorescences held above and beyond the foliage on strong peduncles. Composite inflorescence form, radially symmetrical, with elliptical ray florets and disc florets massed at the center; ray and disc florets develop acropetally on a capitulum. Inflorescences not persistent. Inflorescences face mostly upright. Freely flowering habit, about 60 to 120 inflorescence buds and open inflorescences per plant.

*Flowering response.*—Plants flower continuous and freely from April to October in Germany.

*Postproduction longevity.*—Inflorescences maintain good color and substance for about five days on the plant.

*Fragrance.*—None detected.

*Inflorescence bud.*—Length: About 1 cm. Diameter: About 1.1 cm. Shape: Rounded. Color: Close to 146A.

*Inflorescence size.*—Diameter: About 6 cm. Depth (height): About 2 cm. Disc diameter: About 1.5 cm.

*Ray florets.*—Length: About 2.5 cm. Width: About 8 cm. Shape: Elliptical. Apex: Obtuse. Base: Acute, fused into a tube. Margin: Entire. Texture, upper and lower surfaces: Smooth, glabrous; velvety. Number of ray florets per inflorescence: About 20 to 25 in one to two whorls. Color: When opening and fully opened, upper surface: Longitudinal stripes, 75A and 72A. When opening and fully opened, lower surface: Longitudinal stripes, 75A and 59A; towards the base, 12C.

*Disc florets.*—Shape: Tubular, elongated. Apex: Five-pointed. Length: About 5 mm. Width: About 1 mm. Number of disc florets per inflorescence: About 70. Color: Close to 79A.

*Phyllaries.*—Length: About 1 cm. Diameter: About 2 mm. Shape: Lanceolate. Apex: Acuminate. Base: Truncate. Margin: Entire. Texture, upper and lower surfaces: Smooth. Number per inflorescence: About 14. Color, upper and lower surfaces: Close to 146A.

*Peduncles.*—Length: About 12 cm. Diameter: About 3 mm. Strength: Strong; flexible. Texture: Smooth. Color: Close to 146A.

*Reproductive organs.*—Androecium: Present on disc florets only. Stamen arrangement: Fused around style. Anther shape: Oblong. Anther length: About 2 mm. Anther color: 93A. Pollen amount: Abundant. Pollen color: Yellow. Gynoecium: Present on both ray and disc florets. Stigma shape: Two-parted. Stigma color: 79A. Style length: About 1 mm. Style color: 79A. Ovary color: 79A.

*Seeds.*—Length: About 7 mm. Diameter: About 3 mm. Color: Dark brown.

Disease/pest resistance: Resistance to pathogens and pests common to *Osteospermums* has not been observed on plants grown under commercial greenhouse conditions.

Temperature tolerance: Plants of the new *Osteospermum* have been observed to tolerate temperatures from about 0° C. to about 35° C.

It is claimed:

1. A new and distinct cultivar of *Osteospermum* plant named 'KLEO04110', as illustrated and described.

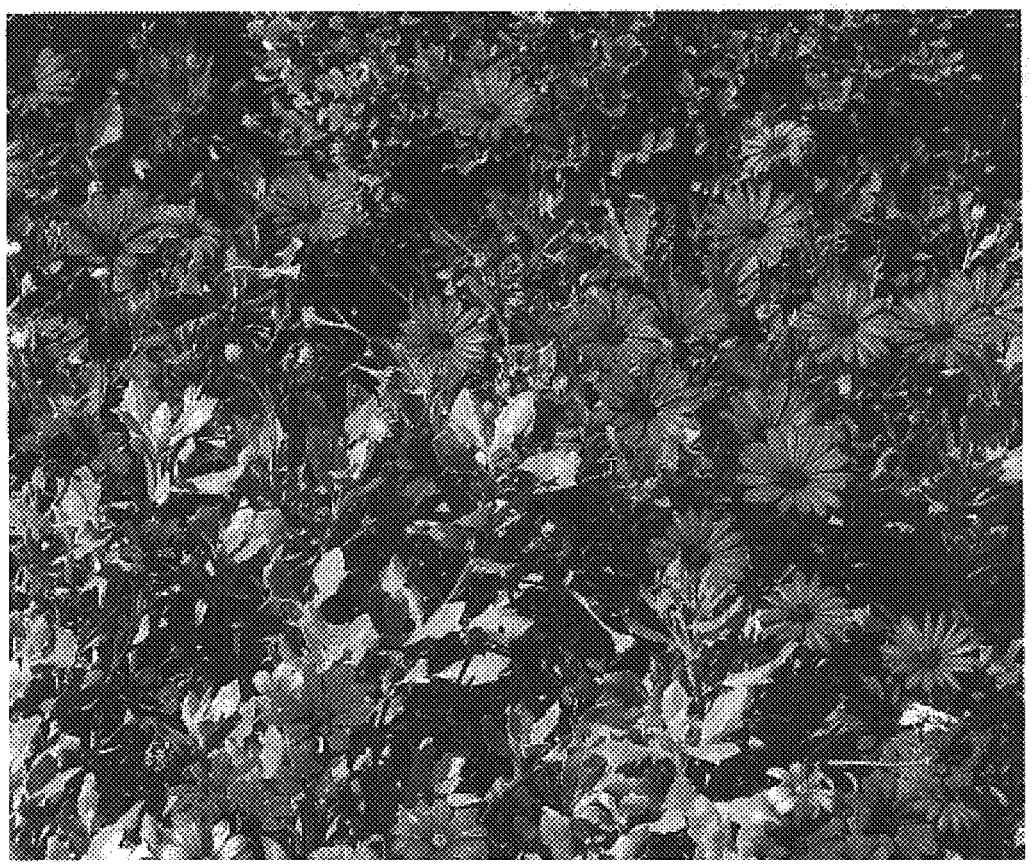

* * * * *